(12) United States Patent  
Portney (10) Patent No.: US 6,197,058 B1
(45) Date of Patent: Mar. 6, 2001

(54) CORRECTIVE INTRAOCULAR LENS SYSTEM AND INTRAOCULAR LENSES AND LENS HANDLING DEVICE THEREFOR

(76) Inventor: Valdemar Portney, 11940 N. Riviera, Tustin, CA (US) 92782

( * ) Notice: Subject to any disclaimer, the term of this patent is extended or adjusted under 35 U.S.C. 154(b) by 0 days.

(21) Appl. No.: 09/273,478

(22) Filed: Mar. 22, 1999

(51) Int. Cl.[7] .................................................. A61F 2/16
(52) U.S. Cl. ...................... 623/6.34; 623/6.32; 623/6.43; 623/6.36; 623/6.12
(58) Field of Search ................................. 623/6.11, 6.12, 623/6.17, 6.18, 6.2, 6.21, 6.32, 6.33, 6.35, 6.36, 6.43, 6.56, 6.34; 606/107

(56) References Cited

U.S. PATENT DOCUMENTS

| 4,932,971 | | 6/1990 | Kelman . | |
|---|---|---|---|---|
| 4,963,148 | | 10/1990 | Sule et al. . | |
| 5,019,097 | | 5/1991 | Knight et al. . | |
| 5,026,396 | | 6/1991 | Darin . | |
| 5,030,231 | * | 7/1991 | Portney ................................. | 623/6.11 |
| 5,041,134 | | 8/1991 | O'Donnell . | |
| 5,044,743 | * | 9/1991 | Ting ..................................... | 623/6.34 |
| 5,133,750 | * | 7/1992 | Momose et al. ..................... | 623/6.11 |
| 5,171,320 | | 12/1992 | Nishi . | |
| 5,222,981 | * | 6/1993 | Werblin .............................. | 623/6.34 |
| 5,258,025 | | 11/1993 | Fedorov et al. . | |
| 5,358,520 | * | 10/1994 | Patel ................................... | 623/6.34 |
| 5,366,502 | | 11/1994 | Patel . | |
| 5,476,513 | * | 12/1995 | Brady et al. ....................... | 623/6.11 |
| 5,480,428 | | 1/1996 | Fedorov et al. . | |
| 5,628,798 | | 5/1997 | Eggleston et al. . | |
| 5,928,245 | * | 7/1999 | Wolf .................................... | 606/107 |
| 5,968,094 | * | 10/1999 | Werblin et al. ..................... | 623/6.34 |
| 6,001,107 | * | 12/1999 | Feingold ............................. | 606/107 |

* cited by examiner

*Primary Examiner*—David H. Willse
*Assistant Examiner*—Suzette J. Jackson
(74) *Attorney, Agent, or Firm*—Howard R. Lambert (57) ABSTRACT

A corrective intraocular lens system comprises a primary intraocular lens for implanting into an individual's aphakic or phakic eye. The primary intraocular lens includes an optic portion having an optical axis and an anterior surface and a posterior surface, and includes attachment means for maintaining the optic portion centered along the optical axis of the individual's eye. The optic portion is formed having a narrow recess or groove formed into the anterior surface adjacent peripheral regions of the optical portion. The recess may extend completely or only partially around the optic. Included is an elastically deformable, corrective secondary intraocular lens having an optic portion with an anterior surface and a posterior surface. The secondary intraocular lens, which provides spherical, cylinder and/or add power to the primary intraocular lens, is formed having a peripheral edge attachment region or edge tab attachment sized to fit into the recess formed in the primary intraocular lens so that secondary intraocular lens is detachably attached to the primary intraocular lens without clamping or any other attachment with the secondary intraocular lens lying along the anterior surface of the primary intraocular lens. Separate primary and secondary intraocular lenses are disclosed as is a device for implanting and extracting a secondary intraocular lens.

49 Claims, 6 Drawing Sheets

CORRECTIVE INTRAOCULAR LENS SYSTEM AND INTRAOCULAR LENSES AND LENS HANDLING DEVICE THEREFOR

BACKGROUND OF THE INVENTION

1. Field of the Invention

The present invention relates generally to the field of ophthalmics, more particularly to ophthalmic devices, and still more particularly to ophthalmic devices known as intraocular lenses (IOLs).

2. Background Discussion

At the onset it may helpful to the understanding of the present invention to define the terms "phakic" and "aphakic" as relate to human eyes. The term "phakic" is applied to an eye in which the naturals ocular lens—whatever its condition—has not been removed. In contrast, the term "aphakic" is applied to an eye from which the natural ocular lens has—for any reason—been removed. In this regard, a phakic eye is considered a dynamic or active eye because the natural lens is subject to change over time. In contrast, an aphakic eye is considered a static eye because the natural lens has been removed.

Vision in an eye is enabled by the cornea and the natural lens (and/or an implanted IOL) located posterior of the cornea, both or all of which refract light from a viewed image to the retina of the eye.

One serious and relatively common vision problem is reduced or complete loss of sight due to the natural ocular lens becoming cloudy or opaque—a condition referred to as cataract. The formation of cataracts is most often associated with natural bodily aging processes—perhaps caused or aggravated by long-term exposure to ultraviolet rays from the sun. In any case, most individuals over the age of about 60 years suffer from cataracts at least to some extent.

The current state of ophthalmics, as far as is known to the present inventor, is that cataracts cannot be cured or reversed, nor can the cataract formation process be significantly arrested. Consequently, when a natural lens becomes so cloudy by cataracts (or by any other mechanism) that the lens can no longer effectively refract light from a viewed image to the retina, thereby significantly impairing vision, the corrective action involves the surgical removal of the natural lens. In this manner, a phakic eye becomes an aphakic eye.

After the defective natural lens has been surgically removed, the common current practice is to implant in the individual's aphakic eye an artificial lens called an intraocular lens or IOL. Previously, thick, high diopter spectacles were prescribed for aphakic eyes, such spectacles however being generally disliked by most patients for obvious reasons.

Intraocular lenses are constructed from bio-compatible optical materials and are, to the extent possible, configured to provide the optical characteristics (with the current exception of accommodation) of the removed natural lens in its prior healthy condition.

IOLs are generally considered to have become practical as a result of the World War II discovery by Dr. Peter Ridley that shards of damaged British fighter aircraft canopies made of PERSPEX (i.e., PLEXIGLAS)—an optically clear, hard poly-methyl methacrylate (PMMA) plastic material—embedded in pilots' eyes caused no adverse reaction in the eyes.

As a result of this discovery, hard, rigid IOLs were constructed from an optical grade of PMMA. These rigid IOLs were compatible with then-current surgical procedures used for removing natural lenses in one piece. That is, the PMMA IOLs could be implanted through the relatively large, 5–6 mm, ocular incisions made for removal of the natural lenses.

Subsequently in the early 1970's Dr. Charles Kelman developed a lens-removal procedure utilizing ultrasound to break up natural lenses. This enabled the natural lenses to be extracted with an irrigating fluid in an emulsified condition from the eye through a much smaller ocular incision than that previously needed to extract the natural lens in one piece. This advantageously resulted in reduced patient trauma and patient recovery time.

This new surgical procedure, called phacoemulsification, created a need for elastically-deformable IOLs that could be rolled or folded for insertion into the eye through the same small ocular incision used in the phacoemulsification lens removal procedure, and which then unfolded to their original shape once in the eye. Such deformable IOLs are commonly constructed from an optically clear, high refractive index, biocompatable silicone or acrylic material.

In addition to the implanting of IOLs in aphakic eyes to restore vision after removal of the natural lens, there has recently been an interest in implanting IOLs in phakic eyes to correct vision deficiencies even with healthy natural lenses. The implanting of IOLs in phakic eyes is an often-attractive alternative to some individuals to the wearing of corrective spectacles or contact lenses or having such corneal surgical procedures as radial keratomy (RK) or photo-radialkeratectomy (PRK) performed.

In an aphakic eyes, an IOL is now most commonly implanted in the posterior chamber of the eye in the general location from which the natural lens was removed. Nevertheless, the implanting of an IOL in the anterior chamber is sometimes necessary because, for example, of damage to the posterior wall of the capsular bag during removal of the natural lens. In contrast, an IOL for a phakic eye is most commonly implanted in the anterior chamber of the eye, but may sometimes be implanted in the posterior chamber or on top of the natural crystaline lens.

Regardless of the reason for the implanting of an IOL or the location of the implanted IOL, a principal objective of the present invention is to provide an IOL system in which corrections to IOL spherical, cylindrical and/or add power can be easily made with minimal invasive action.

SUMMARY OF THE INVENTION

In accordance with the present invention, there is provided a corrective intraocular lens system which comprises a primary intraocular lens for implanting into an individual's aphakic or phakic eye and a thin, elastically deformable, corrective secondary intraocular lens.

The primary intraocular lens includes an optic portion having an optical axis and an anterior surface and a posterior surface, and includes attachment means for maintaining the optic portion optical axis centered along the optical axis of the individual's eye. The primary IOL optic portion is formed having a narrow recess or groove region formed into the anterior surface adjacent to peripheral regions of the optic portion.

The secondary IOL has an optic portion with an anterior surface and a posterior surface. An edge region of the secondary intraocular lens is formed to fit into the primary intraocular lens recess region so that the posterior surface of the secondary intraocular lens lies along the anterior surface of the primary intraocular lens and is sized for inserting into an individual's eye through an ocular incision no greater than about 2.5 millimeters. The secondary intraocular lens is formed from an elastic material such as a silicone (Dr acrylic material.

In accordance with a preferred embodiment of the invention, the primary intraocular lens recess region has a width of about 0.2 mm and a depth of about 0.2 mm to about 0.9 mm. In a variation embodiment, recess region of said primary intraocular lens is. formed having a concave upper surface and a concave lower surface. In another, the recess region of the primary intraocular lens is formed having an overhang region with a uniform thickness. The recess region of the primary intraocular lens may extend all or only partially around the primary intraocular lens optic.

The primary intraocular lens preferably has a spherical diopter power between about −10 and about +35, a cylindrical diopter power between about 0.0 and about +10.0, and/or an add diopter power between about 0.0 and about +4.0. Further, the primary intraocular lens may be a posterior chamber intraocular lens or the optic thereof may be configured for implanting in the anterior chamber of an eye.

It is preferred that the secondary IOL has a spherical diopter power between about −3.0 and about +3.0, a cylinder diopter power between about −5.0 and about +5.0, and/or an add diopter power between about +1.0 and about +4.0. Further, the secondary intraocular lens preferably has a center thickness between about 0.1 mm and about 0.2 mm, and the edge attachment region of the secondary IOL may extend at least substantially around the periphery of said secondary intraocular lens or may comprise at least one radially extending tab preferably formed having at least one transverse groove defining a bend line. In any event the secondary intraocular lens is preferably formed having at least one positioning hole formed in the edge attachment region.

Individually, there is provided an intraocular lens for implanting into an individual's aphakic or phakic eye. The intraocular lens comprises an optic portion having an optical axis and an anterior surface and a posterior surface, and includes attachment means for maintaining the optic portion optical axis centered along the optical axis of the individual's eye. The optic portion is formed having a narrow recess region formed into the anterior surface adjacent to peripheral regions of the optic portion.

The recess region is configured for receiving an edge region of a thin, flexible corrective intraocular lens and thereby detachably attaching the corrective intraocular lens to the intraocular lens to provide power correction thereto.

Preferably, the intraocular lens recess region has a width of about 0.2 mm and a depth of about 0.2 mm to about 0.9 mm. The intraocular lens recess region may be formed having a concave upper surface and a concave lower surface or having an overhang region of uniform thickness. In addition, the intraocular lens recess region may extend around the intraocular lens optic.

The intraocular lens may have a spherical diopter power between about −10 and about +35, a cylindrical diopter power between about 0.0 and about +10.0, and/or an add diopter power between about 0.0 and about +4.0.

Further, the intraocular lens optic may be a posterior chamber intraocular lens or the optic of the intraocular lens may be configured for implanting in the anterior chamber of an eye.

Further comprising the system may be a secondary IOL handling device which includes an elongate, slender pin having means for engaging a secondary intraocular lens and control means connected for rotating the pin in a first rotational direction causing the secondary intraocular lens to become wrapped around said pin and for rotating the pin in a second rotational direction causing a secondary intraocular lens wrapped around the pin to unwrap from the pin.

Included in the handling device is an elongate, thin shield and means connected for axially moving the shield between a first, extended position in which at least portions of the shield extend over a secondary intraocular lens wrapped around the pin and a second, retracted position in which the shield does not extend over a secondary intraocular lens wrapped around the pin. The shield is formed from a biocompatible, elastomeric material, preferably a silicone material.

At least portions of the shield are generally semicylindrical in shape and side edges thereof are preferably flared outwardly.

The means for engaging a secondary intraocular lens includes a protuberance formed on the pin, the protuberance being located and sized to fit into a positioning hole formed in the secondary intraocular lens.

There is also individually provided an elastically deformable intraocular lens having an optic portion with a convex anterior surface and a concave posterior surface, such intraocular lens having an overall dimension not exceeding about 7 mm and a center thickness not exceeding about 0.4 mm. The elastically deformable intraocular lens is formed having a peripheral edge attachment region sized to fit into a narrow recess region formed in a primary intraocular lens optic. This causes the posterior surface of the elastically deformable intraocular lens to lie along an anterior surface of the primary intraocular lens optic so that the elastically deformable intraocular lens provides a power correction to the primary intraocular lens optic.

The elastically deformable intraocular lens is formed for inserting into an individual's eye through an ocular incision no greater than about 2.5 millimeters and may be formed from a silicone material or from an acrylic material. Further, the elastically deformable intraocular lens may have a spherical diopter power between about −3.0 and about +3.0, a cylinder diopter power between about −5.0 and about +5.0 and/or an add diopter power between about +1.0 and about +4.0.

The elastically deformable intraocular lens preferably has a center thickness between about 0.1 mm and about 0.2 mm and the edge attachment region extends at least substantially around the periphery of the elastically deformable intraocular lens. Alternatively, the edge attachment region may comprise at least one radially extending tab, and the tab may be formed having at least one transverse groove defining a bend line. There may be included at least one positioning hole formed in said edge attachment region.

There may individually be provided a handling device for implanting a thin intraocular lens into and extracting a thin intraocular lens from a patient's eye. The handling device comprises an elongate slender pin having means for engaging a thin intraocular lens; and means connected for rotating the pin in a first rotational direction to cause an engaged intraocular lens to become wrapped around the pin and for rotating the pin in a second rotational direction to cause an intraocular lens wrapped around the pin to become unwrapped from the pin.

Included is an elongate thin shield and means connected to the shield for moving the shield between a first axial position in which at least regions of the shield extend over an intraocular lens wrapped around the pin and a second axial position in which the shield does not extend over an intraocular lens wrapped around the pin.

BRIEF DESCRIPTION OF THE DRAWINGS

The present invention can be more readily understood by a consideration of the following detailed description when taken in conjunction with the accompanying drawings, in which:

FIG. 1 is a simplified vertical cross sectional drawing of a human eye.

FIG. 9 is a sequence of pictorial drawings depicting the primary IOL implanted in the posterior chamber of an aphakic eye and showing the insertion of the secondary IOL into the eye and into the receiving recess or channel formed in the primary IOL.

In the various FIGS., the same elements and features are given the same reference numbers

DESCRIPTION OF THE PREFERRED EMBODIMENT

Figure 1A:
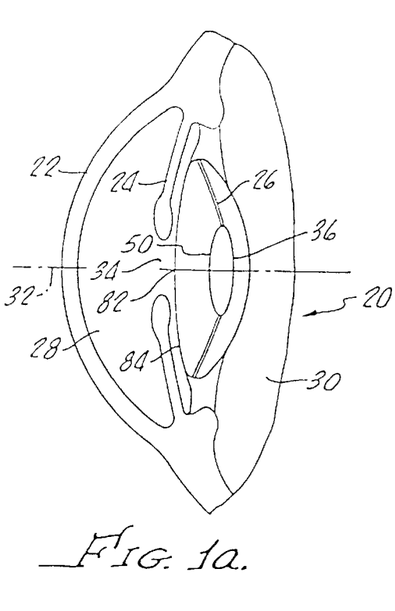
FIG. 1a depicting a typical aphakic eye and showing a representative type of posterior chamber IOL implanted in the posterior chamber from which the natural lens has been removed.
Figure 1B:
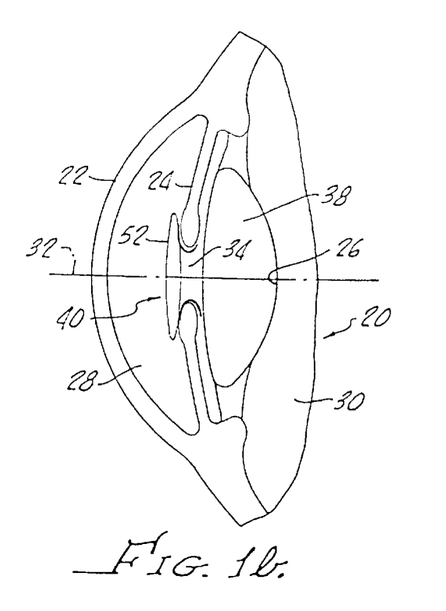
FIG. 1b depicting a typical phakic eye and showing a representative type of IOL implanted in the anterior chamber forwardly of the natural lens in the posterior chamber.

There is shown in FIGS. 1a and 1b, principally for reference purposes, a simplified cross sectional view of forward regions of a representative human eye 20. Comprising eye 20 are a cornea 22, an iris 24, a posterior chamber 26, and an anterior chamber 28. A vitreous humor 30 is contained in eye 20 rearwardly of posterior chamber 26. Eye 20 is further shown having an optical axis 32 that passes through cornea 22, an iris opening 34, and anterior and posterior chambers 28 and 26.

In particular, FIG. 1a depicts eye 20 as an aphakic eye in which a posterior chamber IOL 36 is implanted in posterior chamber 26 from which the natural lens has been removed. FIG. 1b, on the other hand, depicts eye 20 as a phakic eye with a natural lens 38 shown remaining in its normal position in posterior chamber 26. FIG. 1b additionally shows an IOL 40 implanted in the anterior chamber 28 of eye 20 forward of natural lens 38.

As further shown in FIG. 1a optical axis 32 of eye 20 passes through the center of an optic 50 of posterior chamber IOL 36; and as shown in FIG. 1b the optical axis passes through the centers of both an optic 52 of anterior chamber IOL 40 and natural lens 38.

The spherical, cylindrical and/or add power of an IOL to be implanted in a patient's eye is selected by the ophthalmologist in the case of an aphakic eye to restore as closely as possible normal vision and in the case of a phakic eye to correct the patient's vision.

It will be appreciated that determining the exactly correct power of the IOL to be implanted is often difficult because of such factors as the current condition of the patient's eye and effects of the surgical procedure. Consequently, an IOL diopter with a small add power may be selected, even if not actually needed.

Moreover, even if an IOL with an optimum diopter power is implanted, the condition of the patient's eye may deteriorate, for example as the patient ages, such that the IOL diopter is no longer optimum. Furthermore, the actual axial position of the implanted IOL may be slightly different than the intended axial position, thereby introducing an error in the "effective" power of the IOL. In addition, a non-spherical, i.e., cylindrical, cornea can reduce image quality further.

Thus, for whatever reason, the initially selected power of the implanted IOL may not initially, or at some future time, provide the optimum vision or intended vision correction for the patient. To provide the needed or desired power correction, spectacles or contact lenses could be provided but that would tend to obviate the advantages provided by the implanted IOL.

On the other hand, the explanting of the non-optimum IOL and the implanting of another IOL in its place would involve significant surgical intervention with no guarantee that the new IOL would provide the desired correction.

The in situ correction of the power of an already implanted IOL is, therefore, highly desirable in many circumstances, and is the focus of the present invention.

Figure 2:
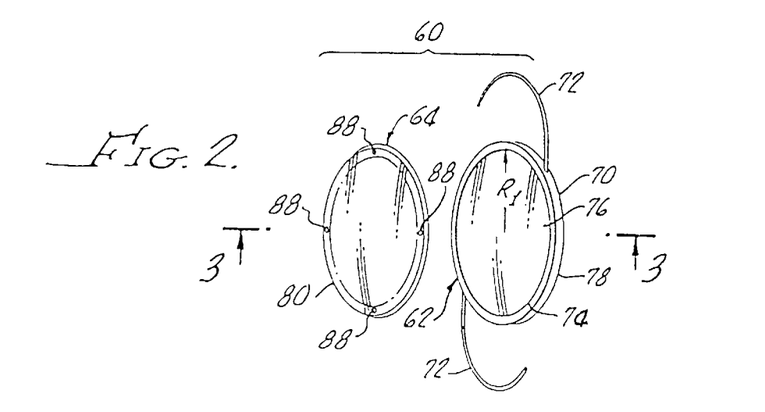
FIG. 2 is a perspective drawing of the intraocular lens (IOL) system of the present invention, showing a primary IOL having an optic to which is attached an opposing pair of filament-type fixation elements (haptics), and showing a thin, contact lens-like secondary or supplemental IOL configured for detachable attachment to the primary IOL to provide a predetermined diopter power correction thereto.
Figure 3:
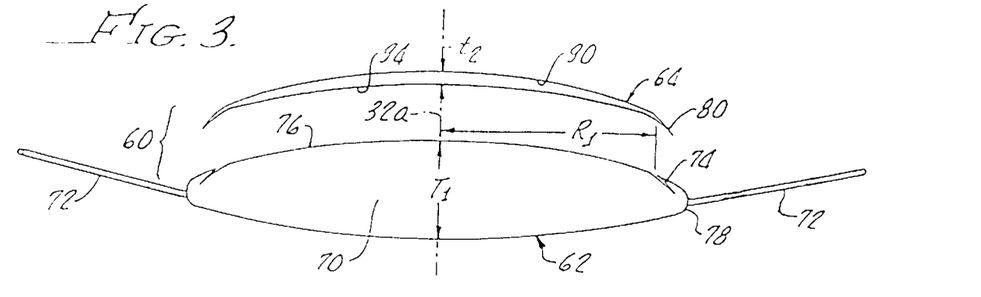
FIG. 3 is a transverse cross sectional drawing taken along line 3—3 of FIG. 2 showing the secondary IOL in close proximity to the anterior surface of the primary IOL, but not yet attached thereto.
Figure 4:
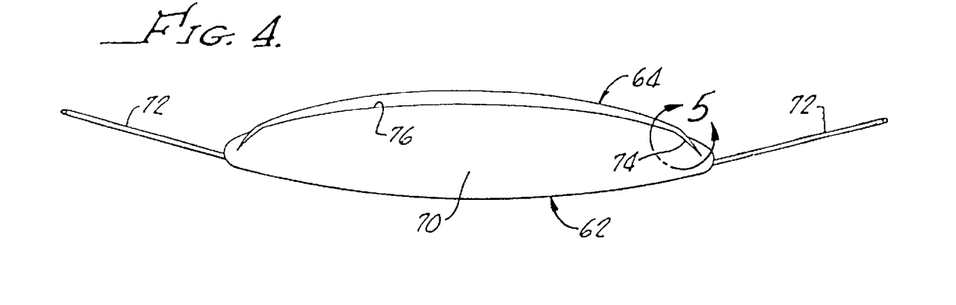
FIG. 4 is a FIG. similar to FIG. 3, except that the secondary IOL is shown detachably attached to a peripheral recess or channel formed into the anterior surface of the primary IOL optic.

To this end, and as best shown in FIGS. 2–4, the present invention comprises an IOL system 60 that includes a primary IOL 62 and a secondary IOL 64 which are configured so the secondary IOL can be readily attached to and detached from the implanted primary IOL, with minimal surgical intervention to the patient, and without disrupting the position of the primary IOL in the eye.

Primary IOL 62 is thus configured to provide the principal vision correction and may be provided in about eighty percent (80%) of cases in the range of between about −1.0 and about +1.0 diopters. The error is most significant for short (i.e., ≦about 20 mm) or long (i.e., ≧about 25 mm) eyes. In any event, primary IOL 62 may be provided with a spherical power of between about −10 and +35 diopters; a cylinder power of between about 0.0 and about +10 diopters; and/or an add power of between about 0 and about +4.0 diopters.

Since secondary IOL 64 is configured to provide only a small diopter correction to primary IOL 62, it may be provided in the diopter range of between about +2.5 and about −2.5. In any event, secondary IOL 64 may be provided with a spherical power of between about −3.0 and +3.0 diopters; a cylinder power of between about −5.0 and about +5.0 diopters; and/or an add power of between about +1.0 and about +4.0 diopters.

Primary IOL 62 has a center optic thickness, $t_1$, which may be in the usual range of between about 0.6 mm and about 1.5 mm, and secondary IOL 64 may have a center optic thickness, $t_2$, in the range of only about 0.1 mm and about 0.2 mm.

With no limitation being intended or implied, primary IOL 62 is disclosed herein as being a posterior chamber IOL (corresponding generally to above mentioned posterior chamber IOL 36). It is, however, to be understood that primary IOL 62 may alternatively be configured for optic 70 thereof to be implanted in the patient's anterior chamber 28 (thereby corresponding generally to above mentioned anterior chamber IOL 40). In addition, again with no limitation being intended or implied, primary IOL 62 is disclosed as a non-plate-type IOL.

Thus, as shown in FIGS. 2–4, primary IOL 62, which may be a one piece rigid IOL (e.g., a PMMA IOL) or a three piece foldable IOL (e.g. a silicone or soft acrylic IOL), comprises an optic or optic region 70 to which is attached an opposing pair of positioning elements, called haptics, 72. These haptics 72 may consist of slender, springy filaments, as shown, or may comprise flexible plates (not shown), both as are common in the IOL field.

To enable detachable attachment of secondary IOL 64 to primary IOL 62, primary IOL optic 70 is formed having a narrow recess or groove or channel 74 formed into an optic anterior surface 76 adjacent a peripheral optic edge 78.

Primary IOL annular recess or channel 74, is sized for receiving and releasably retaining a peripheral edge region 80 of secondary IOL 64, which can readily be inserted by an ophthalmic surgeon into the recess or channel with minimal invasive surgery and without changing the position of primary IOL 62, in the manner described below. Recess or channel 74 may have a width, w, of about 0.5 to about 2.0 mm and a depth, d, of about 0.2 to about 0.9 mm.

Although recess or channel 74 is shown in FIG. 2 as extending completely around optic 70 for receiving complete peripheral edge region 80 of secondary IOL 64, it is to be understood that recess or channel 74 may alternatively extend only partially around the optic, and may be provided in one or more angular segments for receiving only portions of the secondary IOL edge.

To avoid or reduce possible visual effects due to recess or channel 74, the recess or channel is preferably located at a radial distance, $R_1$, from an optical axis 32a that causes the recess or channel to be outside the patient's pupil as defined by iris 24.

For an aphakic eye in which primary IOL 62 is implanted in posterior chamber 26, a central, circular opening 82 (capsularexus) is typically surgically cut in an anterior wall 84 of the posterior chamber (FIG. 1a) during the phacoemulsification procedure. The size of opening 82 is ordinarily about 5 to about 6 mm, so that the removal of the natural lens is facilitated and so that anterior wall 84 does not interfere with light transmission to the implanted IOL. Consequently, the primary IOL recess or channel radius, $R_1$, is preferably selected to be somewhat greater than about 3 mm so that recess or channel 74 is located radially outwardly of anterior wall opening 82, and out of the path of light entering eye 20.

Figure 5:
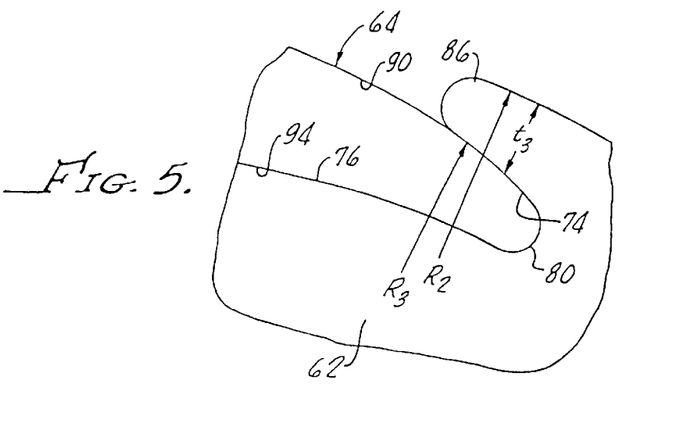
FIG. 5 is a greatly enlarged and detailed transverse cross sectional drawing, in the plane of FIG. 4, of the region in which peripheral regions of the secondary IOL is inserted into the narrow, annular receiving recess or channel formed at an angle in the anterior surface of the primary IOL optic, and showing relative shapes of the edge of the secondary IOL and the mating shape of the receiving recess or channel in the primary IOL.

Nevertheless, there still exists some possibility that glancing rays of light may pass through the region of recess or channel 74 even for a posterior chamber implanted primary IOL 62 and may be greater when the primary IOL is implanted in anterior chamber 28. Therefore, edge 80 of secondary IOL 64 and recess or channel 74 of primary IOL 62 are preferably constructed as shown in FIG. 5 so the edge fits closely into the recess or channel to thereby eliminate or minimize any interior IOL-air interfaces. Moreover, it is preferable that an external radius of curvature, $R_2$, of a lip portion 86 of primary IOL 62 defining recess or channel 74 be made the same as the internal radius of curvature, $R_3$, of the lip portion, i.e., that the lip portion have a constant thickness, $t_3$.

Figure 6:
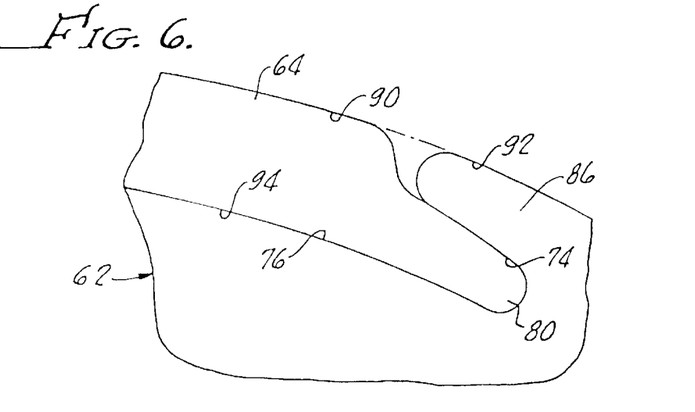
FIG. 6 is a drawing similar to FIG. 5, showing a variation edge shape of the secondary IOL, the edge having a peripheral, thinned edge region.

In the variation depicted in FIG. 6, some optical improvement may be achieved by bulging secondary IOL 64 adjacent edge region 80 so that an anterior surface region 90 of the secondary IOL is substantially in line with or substantially continuous with an exterior surface 92 of primary IOL lip portion 86.

Power of primary IOL 62 is dependent upon anterior and posterior surface curvature, preferably a fixed curvature of anterior surface 76 is provided to maintain a constant arc length for all diopter powers or at least constant for each broad range of diopter power.

Otherwise, except for recess or channel 74, primary IOL is preferably similar to a conventional IOL, and is manufactured by known IOL fabrication processes and may be made of any approved material, size, shape and power.

Secondary IOL 64 is preferably formed having at least one small hole 88 (four such holes being shown in FIG. 2 at ninety-degree intervals) formed relatively adjacent edge 80. By means of hole or holes 88 secondary IOL 64 can easily be positioned in the patients eye 20 and inserting of the edge into primary IOL recess or channel 74 is facilitated.

Secondary IOL 64 is made of a thin, elastically deformable (flexible), biocompatible material and has a convex anterior surface 90 and a concave posterior surface 94 (FIG. 2), to which cylinder correction may be applied. When attached to anterior surface 76 of primary IOL 62, secondary IOL 64 will generally lie along such anterior surface, but is not held or clamped thereto; consequently, any corrective power formed on posterior surface 94 will not be adversely affected.

Although in some respects secondary IOL 64 resembles a conventional contact lens, one principal distinction is that whereas a contact lens has a diameter of about 9 mm for an RGP (rigid, gas permeable) contact lens and a diameter of about 13 to 14 mm for a soft contact lens, secondary IOL 64 has an overall dimension not greater than about 7 mm, (i.e., less than the diameter of primary IOL optic 70). Consequently secondary IOL 64 is best suited for construction by conventional IOL manufacturing processes.

VARIATION SECONDARY IOL OF FIGS. 7–9

As an alternative to secondary IOL 64 being formed having a completely circular edge 80, all of which is inserted, upon attachment to primary IOL recess or channel 74, as described above, the secondary IOL may more preferably be formed having a discontinuous edge resulting in a plurality of projecting edge regions in order to facilitate the attachment of the secondary IOL to primary IOL 62a.

Figure 7:
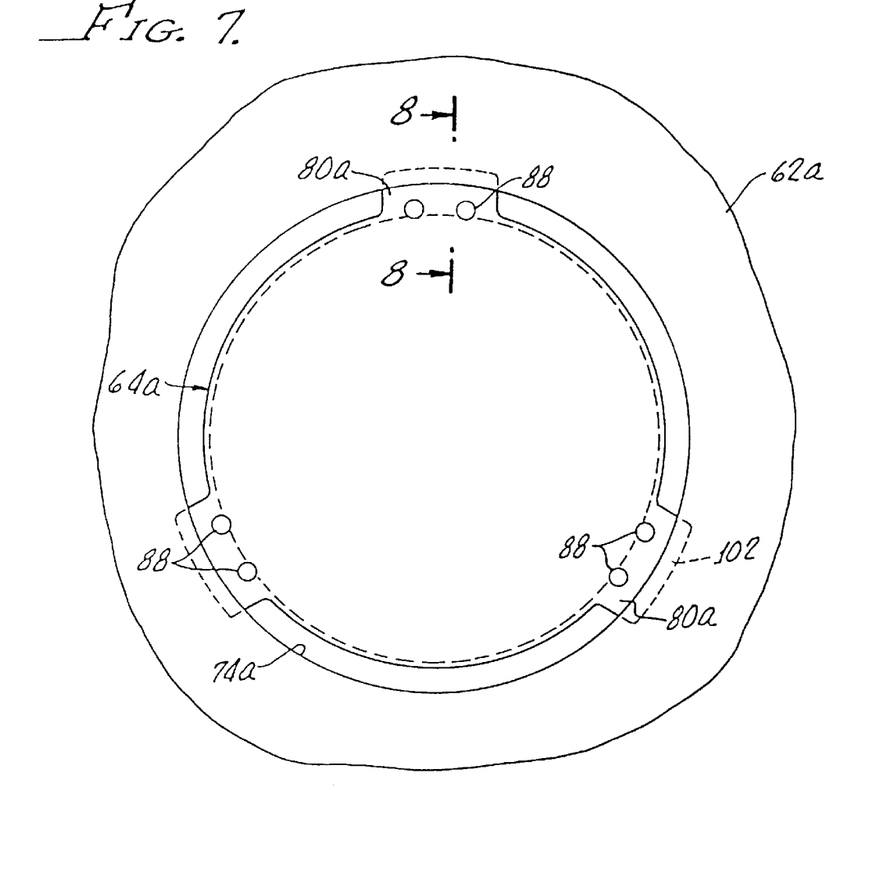
FIG. 7 is a plan view of an alternative configuration of a secondary IOL, in accordance with a variation of the preferred embodiment of the invention, showing the edge of the secondary IOL formed having a plurality (three) radially-extending tabs or ears which are configured for insertion into the receiving recess or channel formed in the primary IOL.

Thus, as depicted in FIGS. 7, a variation secondary IOL 64a is formed having three equally spaced apart edge tabs or ears 80a, each of which is configured for being inserted into a corresponding region of the primary IOL recess or channel. As shown, each such tab 80a is about 25 to about 30 degrees wide. Alternatively, only one such tab 80a may be provided, or any number of such tabs may be provided.

Figure 8:
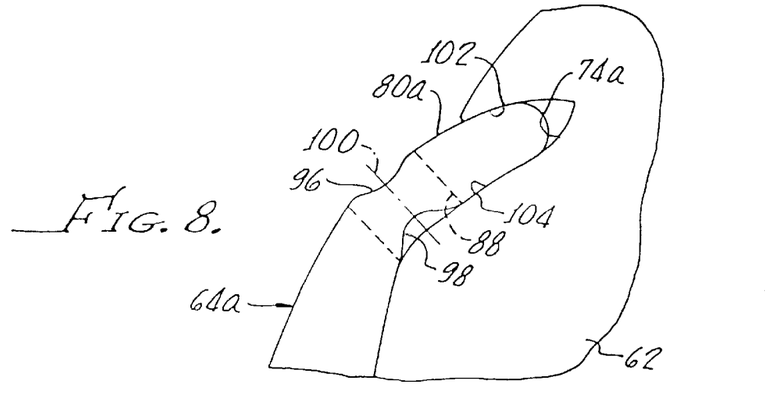
FIG. 8 is a transverse cross sectional drawing taken along line 8—8 of FIG. 7, showing grooves formed across a base region of the secondary IOL tabs to facilitate the inserting of the tabs into the primary IOL receiving recess or channel.

Tabs 80a may, as shown in FIG. 8 for a representative one of the tabs, be formed having a shallow upper transverse groove 96 and/or a shallow lower transverse groove 98 (both grooves being shown by way of example). Groove 96 and/or groove 98 define a bend or hinge line 100 in tabs 80a thereby facilitating the insertion of the tabs (or tab) into recess or channel 74a of primary IOL 62a.

By way of further example, recess or channel 74a of primary IOL 62a may be formed having a concave upper, inner surface 102 and a concave lower, inner surface region 104. Consequently, light entering recess or channel 74a is scattered away from the image focal point of the patient's eye. As above described for recess or channel 74 of primary IOL 62, recess or channel 74a may extend only partially around the primary IOL optic.

In addition, each of tabs 80a is preferably formed having at least one positioning and manipulating holes 88 along bend line 100 (two of such holes being shown in each tab 80a in FIG. 7).

Secondary IOL 64a is detachably attached to primary IOL 62a by tabs (or only a single tab) 80a or, as disclosed above, be edge region 80, and there no pressure applied by the secondary IOL against the primary IOL. Otherwise, secondary IOL 64a is preferably the same as secondary IOL 64 and is constructed in the same manner.

Because of the described method of detachably attaching secondary IOL 64 and 64a to primary IOL 62 and 62a, respectively (i.e., the secondary IOL is only supported in place without any clamping or fastening) the back (posterior) surface shape of secondary IOL 64 or 64a is preserved. As an example, the posterior surface of the secondary IOL can be used for cylinder correction and the anterior surface of the secondary IOL can be used for spherical correction and multifocal power for presbyopia correction.

IMPLANTING AND ATTACHMENT OF SECONDARY IOL (FIG. 9)

FIG. 9 illustrates a technique for implanting a thin, foldable secondary IOL represented by secondary IOL 64 into eye 20 and into detachable attachment to a primary IOL represented by primary IOL 62 of the present invention (that is, an IOL formed having an edge receiving recess or channel 74). For purposes of describing the secondary IOL implanting and attachment process, primary IOL 62 is depicted as an IOL that has been previously implanted in posterior chamber 26.

FIG. 9 depicts, for illustrative purposes and with no limitation being thereby intended or implied, the implanting of secondary IOL 64 and attachment thereof to a posterior chamber-located primary IOL 62 in an aphakic eye. It is, however, to be understood that the technique applies as well to the implanting and the attachment of secondary 64a to primary IOL 62a. Moreover, the technique applies equally to the implanting and attachment of secondary IOL 64 or 64a to primary IOL 62 or 62a of the anterior chamber type previously implanted in anterior chamber 28.

Figure 9A:
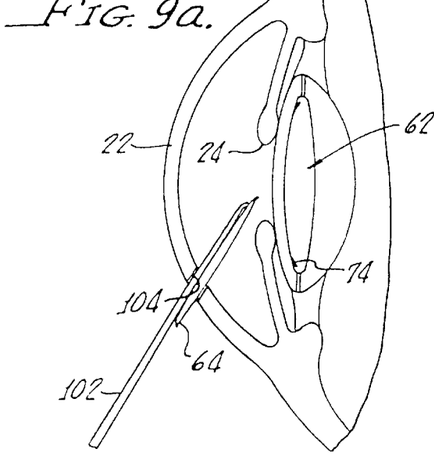
FIG. 9a showing the secondary IOL being inserted by a slender needle through a small corneal incision or hole.

Thus, FIG. 9a depicts secondary IOL 64 being inserted by a slender needle-like implement 102 through a very small hole 104 in cornea 22 (or in the sclera), for example punched by the implement. Since secondary IOL 64 is thin and flexible, it can be inserted through a corneal or sclera hole no larger than about 2.0 to 2.5 mm. The end of implement 102 can advantageously be inserted through IOL edge hole 88.

Figure 9B:
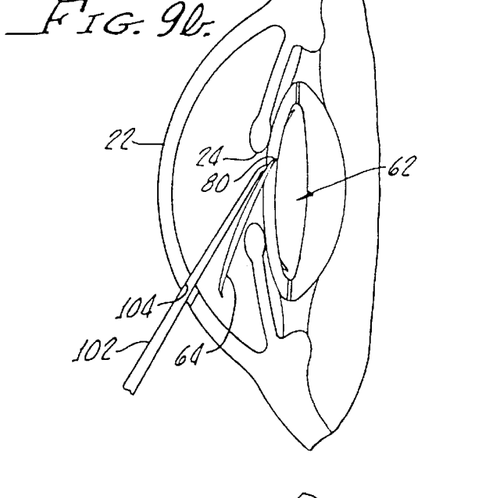
FIG. 9b showing the secondary IOL being then inserted through the pupil and into proximity with the anterior surface of the primary IOL.
Figure 9C:
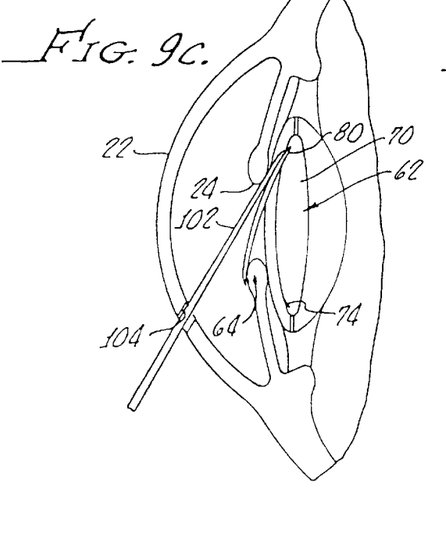
FIG. 9c showing an edge portion of the secondary IOL being inserted or tucked into the receiving recess or channel formed in the anterior surface of the primary IOL optic.
Figure 9D:
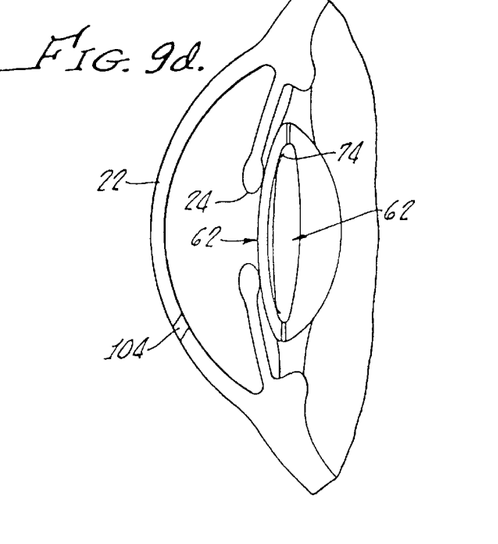
FIG. 9d showing the edge of the secondary IOL fully inserted into the mating primary IOL recess or channel to thereby detachably attach the secondary IOL to the anterior surface of the primary IOL.

In FIG. 9b, secondary IOL 64 is shown inserted entirely through corneal hole 104 and partially through the patient's pupil, and into proximity with primary IOL 62. FIG. 9c depicts upper regions of edge 80 of secondary IOL 64 being inserted or tucked into primary IOL recess or channel 74. In turn, FIG. 9d depicts secondary IOL edge 80 entirely inserted into primary IOL recess or channel 74 with the secondary IOL (actually, posterior surface 94 thereof) in contact with primary IOL anterior surface 64, and with implement 102 having been removed from eye 20.

In the event replacement of secondary IOL 64 becomes desirable or necessary, for example, to implant a secondary IOL of a different power (spherical, cylinder or add), the detaching of the secondary IOL from primary IOL 62 and removal of the secondary IOL from eye 20 is easily accomplished by reversing the implanting procedure described above. Alternatively, after detachment of secondary IOL 64 from primary IOL 64, the secondary IOL can be cut or torn into several pieces for easier removal from the eye.

In the described manner, secondary IOL 64 can be replaced by a different secondary IOL of different power can easily, and with minimal patient trauma, be implanted and attached to primary IOL 62 as an attached secondary IOL no longer provides the desired correction power.

Presbyopic correction of a dynamic phakic eye may, as an illustration, require the implanting of a two or more successive secondary IOLs of progressively increased add during a period of about 10 to 15 years as the patient's eyes change with increased age. As a nonlimiting example, a first secondary IOL implant of about 1.25 diopter power may be required for early presbyopes. A second secondary IOL implant of about 1.75 diopter power may subsequently be required in about 5 to 7 years after the first implant. A third secondary IOL implant of about 2.25 diopter power may subsequently be required in another 5 to 7 years.

It is further to be understood that primary IOL 62 or 62a (or equivalent) as above described and of any desired diopter may typically be manufactured independently of the manufacture of secondary IOL 64 or 64a (or the equivalent) and will usually be separately implanted in a phakic or aphakic eye. The desirability of implanting the secondary IOL and detachably attaching it to primary IOL may occur just after the primary IOL is implanted and during the same surgical procedure (to provide an initial correction, sometime later as noted above, or possibly not at all. Nevertheless, the primary IOL would be appropriately configured for the attachment of a secondary IOL of any desired diopter, when the necessity or desirability of doing so arises.

THE SECONDARY IOL HANDLING APPARATUS OF FIGS. 10–14

Although a conventional pin-type instrument 104 may be used for implanting and extracting (explanting) secondary IOL 64 (and 64a) as has been described above relative to FIG. 9, a specialized secondary IOL handling device or apparatus 200 (FIGS. 10–14) is useful for handling (i.e., implanting and extracting) the secondary IOL, especially in the close confines of the anterior chamber of the eye.

Figure 10:
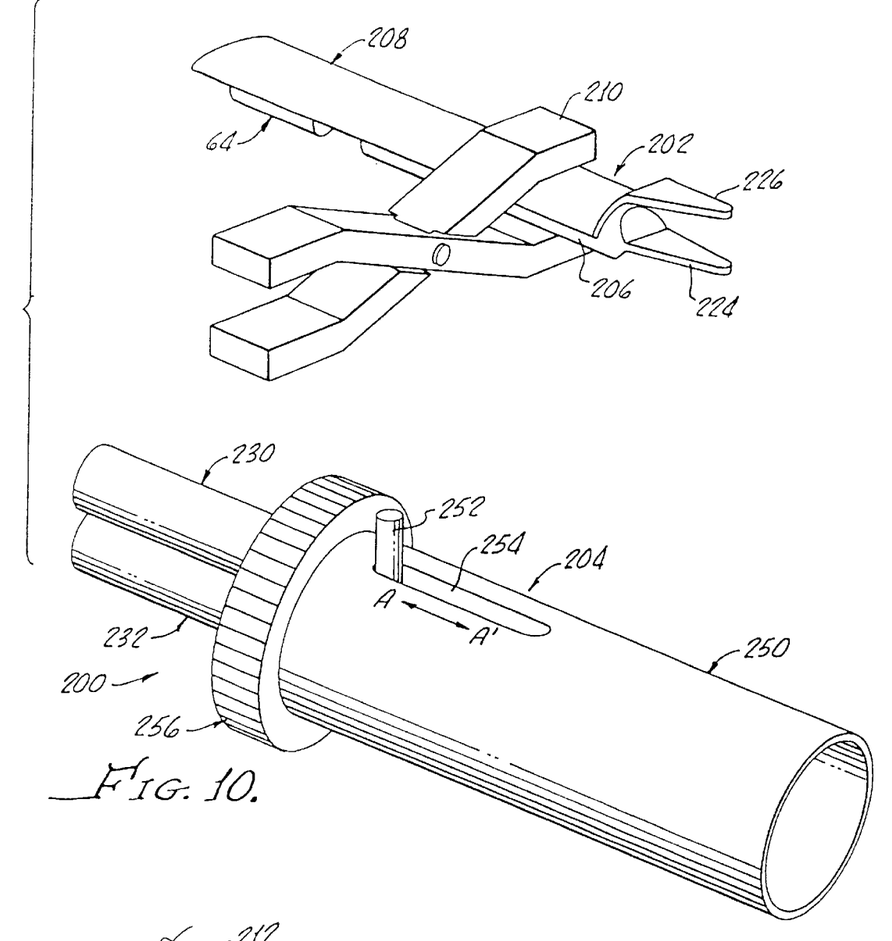
FIG. 10 is a perspective drawing of a handling device or apparatus for implanting a secondary IOL into an eye and for extracting (explanting) a secondary IOL from an eye, showing a first, lens implanting/extracting portion comprising a lens holding pin and a retractable shield and showing an associated second portion for receiving the pin and shield portion and for enabling the rotation of the pin and for extending and retracting the shield.

Shown comprising handling device 200 are a first, pin and shield portion 202 and a second, pin and shield receiving and controlling portion 204 (FIG. 10). Because of concern over the transmission of body fluid-borne diseases, such as AIDS and hepatitis, first portion 202 may be made disposable after a single use. In contrast, second portion 204, which is not expected to come in contact with body fluids, may be made reusable.

Figures 11, 12, 13:
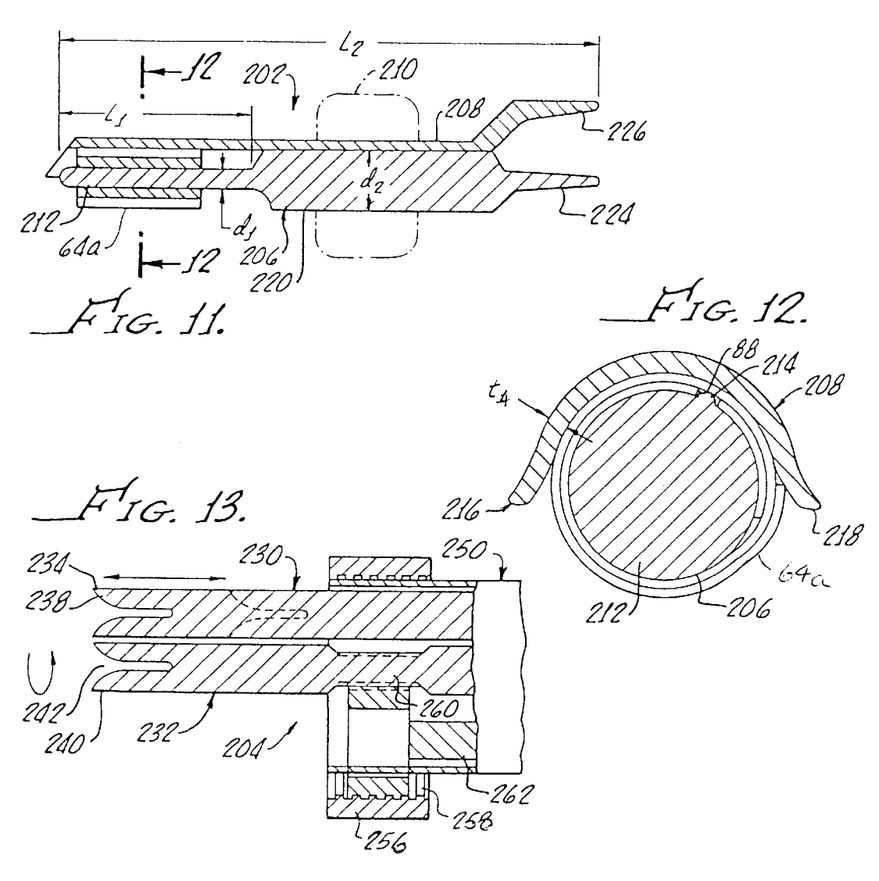
FIG. 11 is a longitudinal cross sectional drawing of the first portion of the handling device of FIG. 10 showing the pin and shield construction thereof, showing a secondary IOL wrapped around a distal end region of the pin and showing the shield extended over the IOL, and further showing attachment proximal end regions of the pin and shield configured for detachably attaching the pin and shield to the second, receiving and control portion.
FIG. 12 is a transverse cross sectional drawing taken along line 12—12 of FIG. 11, showing a secondary IOL wrapped around the distal end of the pin.
FIG. 13 is a longitudinal cross sectional drawing of the second portion of the handling device of FIG. 10, showing a connector region for detachably receiving proximal ends of the pin and shield, and showing a rotary actuator connected for enabling the rotation of the pin when the pin is attached and showing a linear actuator for slidingly extending and retracting the shield when the shield is attached.

Shown comprising first portion 202 are an elongate, rigid pin 206 and a flexible shield 208 (FIGS. 10 and 11). Shown in FIG. 10 is a conventional small clamp 210 that is used to hold pin 206 and shield 208 together until they are installed in second portion 204.

As seen from FIG. 11, an elongate, round distal end region 212 of pin 206 is formed having a uniform diameter, $d_1$, that is only about 0.5 to about 0.8 mm. Length, $L_1$, of pin distal end region 212 is preferably about 8 to 10 mm. Pin 206 may be constructed of a surgical grade of stainless steel or titanium.

A small secondary IOL pin-like engaging projection 214 formed on pin distal end region 212 in a generally central location thereof is sized to fit into the or one of the holes 88 of representative secondary IOL 64a that (PEIG. 12). As shown, secondary IOL 64a (or 64) is then wrapped closely around distal end region 212 in preparation for implanting in an eye and for attachment to primary IOL 62 (or 62a) in the above-described manner. As a non-limiting example, for a pin end region diameter, $d_1$, of about 0.8 mm, and a secondary IOL diameter of between about 5.0 mm to 6.0 mm, secondar IOL 64a (or 64) will wrap around pin end region 212 about twice (as depicted in FIGS. 11 and 12).

Shield 208, which is constructed from an elastomeric material, such as silicone or an acrylic material, is constructed having at least a distal end region 214 that is semi-cylindrical in shape (FIG. 12). Shield end region 216, which is sized to slide axially, in a close fitting relationship, over a secondary IOL 64 (or 64a) wrapped around pin end region 212 to thereby keep the IOL wrapped around the pin end region, preferably has a thickness, $t_4$, of about 0.3 mm. Side edges 218 of shield end region 216 are preferably slightly flared out as depicted in FIG. 12 to provide for sealing the ocular incision (not shown) made for implanting or extracting the secondary IOL.

A central region 220 of pin 206 is made having a diameter, $d_2$, that is about three times the distal end region diameter, $d_1$. A proximal end 224 of pin 206 is tapered in an elongate cone shape (FIGS. 10 and 11). A proximal end 226 of shield 298 is similarly tapered in an elongate cone shape. Overall length, $L_2$, of portion 202 may be from about 15 mm to about 25 mm.

Receiving and control portion 204, as shown in FIG. 13, comprises a linear actuator or means 230 configured for imparting linear, axial movement to shield 208 and a rotary actuator or means 232 configured for imparting rotational movement to pin 206. To this end, a distal end 234 of linear actuator 230 is formed having a conically tapered socket 236 sized to receive proximal end 226 of shield 208 in frictionally locking engagement. Similarly, a distal end 238 of rotary actuator 232 is formed having a conically tapered socket 240 sized to receive proximal end 224 of shield 206 in frictionally locking engagement.

Proximal ends of linear actuator 230 and rotary actuator 232 are retained in a handle-like housing 250. As shown in FIG. 10, linear actuator 230 is moved for advancing and retracting in an axial direction (Arrow A—A') by a lever 252 that protrudes through an elongate slot 254 in housing 250. Rotary actuator 232 is rotated in either rotational direction (Arrow B—B') by a thumb wheel 256 that is interconnected with the rotary actuator by a drive gear 258 that engages a gear 260 formed on the rotary actuator (FIG. 13). Drive gear 258 is mounted on a shaft 262 that is, in turn, mounted in housing 250.

In use, pin proximal end 224 is frictionally connected or coupled to socket 242 of rotary actuator 232 and shield proximal end 226 is frictionally connected or coupled to socket 238 of linear actuator 230. Then, rotational movement of rotary actuator 232, by thumb wheel 256, causes rotation of pin 206. Depending upon the direction of rotation of pin 206, an unwrapped secondary IOL (for example, IOL 62a) engaged by projection 214 is can be wrapped around pin distal end region 212 (as depicted in FIG. 14) for implanting into a patient's eye or a secondary IOL wrapped around the pin distal end can be unwrapped, for example, after the IOL has been inserted into a patient's eye in proximity to an implanted primary IOL.

Figure 14:
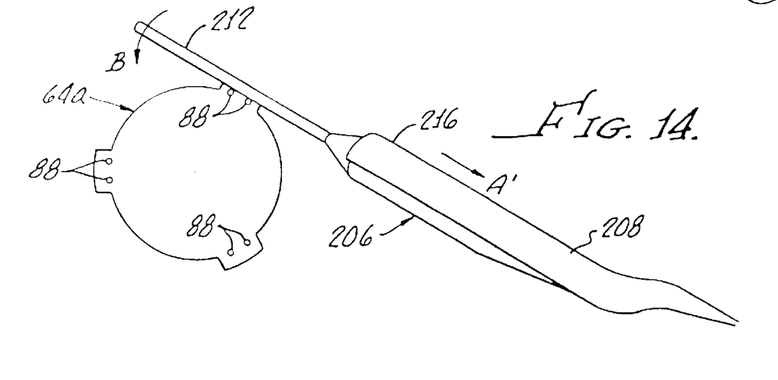
FIG. 14 is a perspective drawing of the first portion of the IOL handling device showing the distal end region of the pin in engagement with a representative secondary IOL in preparation for wrapping the IOL around the pin and showing the shield in its retracted position for enabling such IOL wrapping.

While a secondary IOL is being wrapped around or unwrapped from pin distal end region 212, shield 208 is retracted by operation of lever 252 so that distal end region 214 is out of the way (FIG. 14). After a secondary IOL has been wrapped around pin distal end region 212, shield 208 is advanced by lever 252 so that shield distal end region 214 extends over the wrapped IOL to keep it wrapped.

As device 200 implants a secondary IOL wrapped around pin region 212 through an ocular incision, shield end region 216, which had been extended to cover the wrapped IOL, is retracted so as to stay in and seal the incision.

IOL handling device 200 provides good control over the secondary IOL during its implanting in or extraction from a patient's eye, as is especially needed, for example, when applying the secondary IOL to or removing it from a primary IOL optic located in the anterior chamber of the eye where there exists only minimal clearance between such optic and the sensitive endothelial surface of the cornea.

Importantly, device 200 permits manipulation of the secondary IOL with one hand. A small manipulator-probe (not shown) can be employed by the other hand to assist in unwrapping an inserted secondary IOL and placement thereof into recess 74 or 74a of the implanted primary IOL.

Although there has been described above an IOL pair or system, comprising a primary and a corrective secondary IOL and individual primary and secondary IOLs, as well as a secondary IOL handling device, in accordance with the present invention for purposes of illustrating the manner in which the present invention maybe used to advantage, it is to be understood that the invention is not limited thereto. It is thus within the scope of the present invention that a single IOL manufacturer commercially provide both primary and secondary IOLs, for exampie, in sets, and in any desired number of styles, configurations, materials and diopter powers. On the other hand, it is still within the scope of the invention that an IOL manufacturer may provide only primary IOLs as disclosed above having such recesses or channels 74 or 74a so they can have attached thereto secondary IOLs as described above, even if the secondary IOLs are provided by a different manufacturer. Consequently, any and all variations and equivalent arrangements which may occur to those skilled in the applicable art are to be considered to be within the scope and spirit of the invention as set forth in the claims which are appended hereto as part of this application.

What is claimed is:

1. A corrective intraocular lens system which comprises:
   a. a primary intraocular lens for implanting into an individual's aphakic or phakic eye, said primary intraocular lens including an optic portion having an optical axis and an anterior surface and a posterior surface, and including attachment means for maintaining said optic portion optical axis centered along the optical axis of the individual's eye; said optic portion being formed having a narrow recess region formed into said anterior surface adjacent to peripheral regions of the optic portion; and
   b. an elastically deformable, corrective secondary intraocular lens having an optic portion with an anterior surface and a posterior surface, said secondary intraocular lens being formed having an edge attachment region sized to fit into said primary intraocular lens recess region so as to cause the secondary intraocular lens to lie along the anterior surface of the primary intraocular lens.

2. The corrective intraocular lens system as claimed in claim 1, wherein said secondary intraocular lens is formed for inserting into an individual's eye through an ocular incision no greater than about 2.5 millimeters.

3. The corrective intraocular lens system as claimed in claim 2, wherein said secondary intraocular lens is formed from a silicone material.

4. The corrective intraocular lens system as claimed in claim 2, wherein said secondary intraocular lens is formed from an acrylic material.

5. The corrective intraocular lens system as claimed in claim 1, wherein said primary intraocular lens recess region has a width of about 0.2 mm.

6. The corrective intraocular lens system as claimed in claim 1, wherein said primary intraocular lens annular recess has a depth of about 0.2 mm to about 0.9 mm.

7. The corrective intraocular lens system as claimed in claim 1, wherein said recess region of said primary intraocular lens is formed having a concave upper surface and a concave lower surface.

8. The corrective intraocular lens system as claimed in claim 1, wherein said recess region of said primary intraocular lens is formed having an overhang region having a uniform thickness.

9. The corrective intraocular lens system as claimed in claim 1, wherein the recess region of the primary intraocular lens extends around the primary intraocular lens optic.

10. The corrective intraocular lens system as claimed in claim 1, wherein said primary intraocular lens has a spherical diopter power between about −10 and about +35.

11. The corrective intraocular lens system as claimed in claim 1, wherein said primary intraocular lens has a cylindrical diopter power between about 0.0 and about +10.0.

12. The corrective intraocular lens system as claimed in claim 1, wherein said primary intraocular lens has an add diopter power between about 0.0 and about +4.0.

13. The corrective intraocular lens system as claimed in claim 1, wherein said primary intraocular lens is a posterior chamber intraocular lens.

14. The corrective intraocular lens system as claimed in claim 1, wherein said optic of said primary intraocular lens is configured for implanting in the anterior chamber of an eye.

15. The corrective intraocular lens system as claimed in claim 1, wherein said secondary intraocular lens has a spherical dioplter power between about −3.0 and about +3.0.

16. The corrective intraocular lens system as claimed in claim 1, wherein said secondary intraocular lens has a cylinder diopter power between about −5.0 and about +5.0.

17. The corrective intraocular lens system as claimed in claim 1, wherein said secondary intraocular lens has an add diopter power between about +1.0 and about +4.0.

18. The corrective intraocular lens system as claimed in claim 1, wherein said secondary intraocular lens has a center thickness between about 0.1 mm and about 0.2 mm.

19. The corrective intraocular lens system as claimed in claim 1, wherein said edge attachment region extend at least substantially around the periphery of said secondary intraocular lens.

20. The corrective intraocular lens system as claimed in claim 1, wherein said secondary intraocular lens is formed having at least one positioning hole formed in said edge attachment region.

21. The corrective intraocular lens system as claimed in claim 1, including a secondary IOL handling device.

22. A corrective intraocular lens system which comprises:
   a. a primary intraocular lens for implanting into an individual's aphakic or phakic eye, said primary intraocular lens including an optic portion having an optical axis and an anterior surface and a posterior surface, and including attachment means for maintaining said optic portion optical axis centered along the optical axis of the individual's eye; said optic portion being formed having a narrow recess region formed into said anterior surface adjacent to peripheral regions of the optic portion;

b. an elastically deformable, corrective secondary intraocular lens having an optic portion with an anterior surface and a posterior surface, said secondary intraocular lens being formed having an edge attachment region sized to fit into said primary intraocular lens recess region so as to cause the secondary intraocular lens to lie along the anterior surface of the primary intraocular lens; and c. a secondary IOL handling device including an elongate, slender pin having means for engaging said secondary intraocular lens and control means connected for rotating said pin in a first rotational direction causing the secondary intraocular lens to become wrapped around said pin.

23. The corrective intraocular lens system as claimed in claim 22, wherein said control means is connected for rotating said pin in a second rotational direction causing a secondary intraocular lens wrapped around said pin to unwrap from the pin.

24. The corrective intraocular lens system as claimed in claim 22, wherein said handling device includes an elongate, thin shield and means connected for axially moving said shield between a first, extended position in which at least portions of the shield extend over a secondary intraocular lens wrapped around said pin and a second, retracted position in which the shield does not extend over a secondary intraocular lens wrapped around said pin.

25. The corrective intraocular lens system as claimed in claim 24, wherein said shield is formed from a biocompatible, elastomeric material.

26. The corrective intraocular lens system as claimed in claim 25, wherein said material is a silicone material.

27. The corrective intraocular lens system as claimed in claim 24, wherein said at least portions of said shield are generally semi-cylindrical in shape.

28. The corrective intraocular lens system as claimed in claim 27, wherein side edges of said at least portions of said shield are flared outwardly.

29. The corrective intraocular lens system as claimed in claim 22, wherein said means for engaging a secondary intraocular lens includes a protuberance formed on said pin, said protuberance being located and sized to fit into a positioning hole formed in the secondary intraocular lens.

30. An intraocular lens for implanting into an individual's aphakic or phakic eye, said intraocular lens comprising an optic portion having an optical axis and an anterior surface and a posterior surface, and including attachment means for maintaining said optic portion optical axis centered along the optical axis of the individual's eye; said optic portion being formed having a narrow recess region formed into said anterior surface adjacent to peripheral regions of the optic portion.

31. The intraocular lens as claimed in claim 30, wherein said recess region is configured for receiving an edge region of a thin, flexible corrective intraocular lens and thereby detachably attaching said corrective intraocular lens to said intraocular lens to provide power correction thereto.

32. The intraocular lens as claimed in claim 30, wherein said intraocular lens recess region has a width of about 0.2 mm.

33. The intraocular lens as claimed in claim 30, wherein said intraocular lens recess region has a depth of about 0.2 mm to about 0.9 mm.

34. The intraocular lens as claimed in claim 30, wherein said intraocular lens recess region is formed having a concave upper surface and a concave lower surface.

35. The intraocular lens as claimed in claim 30, wherein said intraocular lens recess region is formed having an overhang region of uniform thickness.

36. The intraocular lens as claimed in claim 30, wherein the intraocular lens recess region extends around the intraocular lens optic.

37. The intraocular lens as claimed in claim 30, wherein said intraocular lens has a spherical diopter power between about −10 and about +35.

38. The intraocular lens as claimed in claim 30, wherein said intraocular lens has a cylindrical diopter power between about 0.0 and about +10.0.

39. The intraocular lens as claimed in claim 30, wherein said intraocular lens has an add diopter power between about 0.0 and about +4.0.

40. The intraocular lens as claimed in claim 30, wherein said intraocular lens optic is a posterior chamber intraocular lens.

41. The primary intraocular lens as claimed in claim 30, wherein said optic of said intraocular lens is configured for implanting in the anterior chamber of an eye.

42. An elastically deformable intraocular lens having an optic portion with a convex anterior surface and a concave posterior surface, said intraocular lens having an overall dimension not exceeding about 7 mm and a center thickness not exceeding about 0.4 mm, said elastically deformable intraocular lens being formed having an edge attachment region sized to fit into a narrow recess region formed in a primary intraocular lens optic anterior surface adjacent to peripheral edge regions of said optic so that the elastically deformable intraocular lens lies along an anterior surface of said primary intraocular lens optic so that the elastically deformable intraocular lens provides a power correction to the primary intraocular lens optic.

43. The elastically deformable intraocular lens as claimed in claim 42, wherein said elastically deformable intraocular lens is formed for inserting into an individual's eye through an ocular incision no greater than about 2.5 millimeters.

44. The elastically deformable intraocular lens as claimed in claim 42, wherein said elastically deformable intraocular lens is formed from a silicone material.

45. The elastically deformable intraocular lens as claimed in claim 42, wherein said elastically deformable intraocular lens is formed from an acrylic material.

46. The elastically deformable intraocular lens as claimed in claim 42, wherein said elastically deformable intraocular lens has a spherical diopter power between about −3.0 and about +3.0.

47. The elastically deformable intraocular lens as claimed in claim 42, wherein said elastically deformable intraocular lens has a cylinder diopter power between about −5.0 and about +5.0.

48. The elastically deformable intraocular lens as claimed in claim 42, wherein said elastically deformable intraocular lens has an add diopter power between about +1.0 and about +4.0.

49. The elastically deformable intraocular lens as claimed in claim 42, wherein said elastically deformable intraocular lens has a center thickness between about 0.1 mm and about 0.2 mm.

* * * * *